United States Patent [19]

Baer

[11] Patent Number: 5,387,833
[45] Date of Patent: Feb. 7, 1995

[54] METHOD AND DEVICE FOR SEPARATING ACOUSTIC WAVE-GENERATED ENERGY FROM DIRECTLY COUPLED ELECTROMAGNETIC INTERFERENCE

[75] Inventor: Richard L. Baer, Los Altos, Calif.

[73] Assignee: Hewlett-Packard Company, Palo Alto, Calif.

[21] Appl. No.: 259,377

[22] Filed: Jun. 14, 1994

Related U.S. Application Data

[63] Continuation of Ser. No. 41,256, Apr. 1, 1993, abandoned.

[51] Int. Cl.⁶ .............................................. H03H 9/145
[52] U.S. Cl. .................................. 310/313 R; 310/316; 333/151; 333/194
[58] Field of Search ................... 310/313 R, 316, 318; 333/150, 151, 194

[56] References Cited

U.S. PATENT DOCUMENTS

| | | | |
|---|---|---|---|
| 3,551,837 | 12/1970 | Speiser et al. | 310/313 R |
| 3,845,418 | 10/1974 | Weglein | 333/30 |
| 3,855,556 | 12/1974 | Hartmann | 310/313 R |
| 4,078,210 | 3/1978 | Lewis | 310/366 |
| 4,221,132 | 9/1980 | Poole | 73/620 |
| 4,247,903 | 1/1981 | Grudkowski et al. | 333/150 |
| 4,333,342 | 6/1982 | Gilden et al. | 310/313 R |
| 4,939,387 | 7/1990 | Popek et al. | 333/150 |
| 5,076,094 | 12/1991 | Frye et al. | 310/313 R |
| 5,111,168 | 5/1992 | Panasik et al. | 333/152 |
| 5,130,257 | 7/1992 | Baer et al. | 436/151 |
| 5,221,871 | 6/1993 | Fuchs et al. | 310/313 R |

FOREIGN PATENT DOCUMENTS 89309266.8  9/1989  European Pat. Off. .

OTHER PUBLICATIONS

Martin, S. J. et al., "Characterization of SH Acoustic Plate Mode Liquid Sensors," *Sensors and Actuators*, 20 (1989), pp. 253–268.

M. Hoummady et al. "Acoustic Wave Viscometer", 1991, vol. 62 (8), pp. 1999–2003, *Rev. Sci. Instrum.*

Akihiro Sawaguchi et al. "Liquid Viscosity Measurement Using SH Wave Propagation . . . ", 1992, vol. 31 (9B), pp. 3094–3097, *Jpn. J. Appl. Phys.*

U. Kaatze et al. "Acoustical Absorption Spectroscopy of Liquids between 0.15 and 3000 MHz . . . ", 1988, vol. 21 (4), pp. 402–406, *J. of Phys. E. Sci. Instrum.*

*Primary Examiner*—Thomas M. Dougherty

[57] ABSTRACT

A method and apparatus in which signal output of an acoustic wave device is separated into desired and undesired components. An excitation signal to an input of the acoustic wave device is periodically interrupted for durations based upon the time required for acoustic waves to travel from the input to the output of the device. The duration of excitation is less than the time required for wave travel, allowing electromagnetic interference to complete its passage to the output before the arrival of acoustic wave energy. The non-simultaneous arrival of electromagnetic interference and acoustic wave-generated energy allows the electromagnetic interference to be gated from the output. Electrical switches are employed, such as double-balanced mixers or PIN diode switches. The period of pulses for providing the interruptions of excitation is at least as great as the sum of the required time for acoustic wave travel and the time during which the device is excited. The switch for gating the output remains open during intervals in which the device is excited.

19 Claims, 9 Drawing Sheets

METHOD AND DEVICE FOR SEPARATING ACOUSTIC WAVE-GENERATED ENERGY FROM DIRECTLY COUPLED ELECTROMAGNETIC INTERFERENCE

CROSS REFERENCE TO RELATED APPLICATION

This is a continuation of copending application Ser. No. 08/041,256 filed on Apr. 1, 1993, now abandoned.

TECHNICAL FIELD

The present invention relates generally to acoustic wave devices and more particularly to increasing the sensitivity of acoustic wave devices.

BACKGROUND ART

Acoustic wave devices are used in a variety of sensing applications. For example, acoustic delay lines can be used to sense environmental factors such as temperature and pressure, and can be used to measure variables such as mass, viscosity and density. Surface acoustic wave (SAW) delay lines have been employed to sense vapors in air by applying a surface film that preferentially binds the vapor to a surface of the SAW device. The surface film traps the vapor, causing a mass increase that changes the phase or amplitude of acoustic waves propagating along a piezoelectric substrate of the device. A surface transverse wave (STW) delay line may be used to sense the concentrations of chemicals in aqueous solutions by immobilizing antibodies on the surface of the STW device, whereupon the net surface mass increases as the antigen that is complementary to the antibodies is captured from the solutions. Again, phase shifts and/or changes in signal amplitude can be monitored to obtain a determination regarding the captured antigen.

Increasing the sensitivity of acoustic wave devices is an ever-present goal in the design of the various types of the devices. In practice, the maximum sensitivity is at least partially determined by the acoustic attenuation of wave propagation. That is, the same components of wave motion that cause an increase in sensitivity increase the attenuation that is experienced by the device. For example, a surface grating of fingers that is used to trap an acoustic wave to an STW device may be increased in thickness in order to improve sensitivity, but the thicker grating will increase the attenuation that results from a surface film or from a fluid to be analyzed.

Eventually a limit is reached at which changes to factors such as the thickness of a preferential surface film cannot be used to increase sensitivity. The limit cannot surpass that point at which increased film thickness will result in a film that causes wave attenuation that renders the device substantially unaffected by any chemical interaction. This limit at which monitoring the output of the device would make it appear that interaction of the device with a substance of interest will not increase wave attenuation is referred to herein as the "attenuation limit." While the attenuation limit has been described with reference to an acoustic wave device having a grating of wave-trapping fingers and a preferential surface film, the importance of the attenuation limit to maximizing the sensitivity of an acoustic wave device applies equally to all other types of acoustic wave devices and applies to the various sensing environments, e.g., the detection of a vapor within air and the determination of the viscosity of a liquid in which the device is immersed.

It is an object of the present invention to provide an acoustic wave device and a method of operating the device that allow further improvements to sensitivity.

SUMMARY OF THE INVENTION

The above object has been met by a method and device that separates the output signal of an acoustic wave device into a desired component of energy that is induced by receiving propagated acoustic waves and an undesired component of energy that is coupled from an input to the output without undergoing acoustic conversion. The undesired component of energy is electromagnetic interference having a variety of sources. One source of electromagnetic interference is electromagnetic radiation from an input transducer to an output transducer of the acoustic wave device. Another source is inter-transducer capacitance.

The method includes selectively interrupting the application of an excitation signal to the input transducer in a manner based upon the time required for acoustic waves to travel from the input transducer to the output transducer. Electromagnetic interference will travel at the speed of light, regardless of the source of the interference. In comparison, acoustic waves propagating through a device substrate, typically a piezoelectric substrate, will travel at sound velocity. Interrupting the excitation signal at the input transducer allows the electromagnetic interference to complete its travel from the input transducer to the output transducer before the acoustic wave energy reaches the output transducer. The output signal from the output transducer can then be gated to reduce the effect of electromagnetic interference on monitoring apparatus.

In a preferred embodiment, the excitation signal is applied at the input transducer for a period slightly shorter than the time in which acoustic wave energy will propagate from the input transducer to the output transducer, so that the device is driven for the maximum percentage of time without causing simultaneous arrival of acoustic waves and electromagnetic interference. A switch is used to then open the path from a source of the input signal to the input transducer. The acoustic wave energy arrives at the output transducer during that time in which the input is interrupted. Following the completion of acoustic wave propagation, the excitation signal is again applied at the input. Thus, the period for switch activation is greater than the sum of the acoustic delay of the device and the time of launching acoustic waves by the application of the excitation signal.

A second switch is applied at the output of the acoustic wave device. This switch disconnects the output transducer from monitoring apparatus during those times in which electromagnetic interference is expected to reach the output transducer. Ideally, the switch is closed only during those time in which the output transducer is receiving acoustic wave energy. This switch is not necessary in some embodiments.

Each of the two switches may be a double-balanced diode ring mixer (DBM). L and R ports of the mixer may be used for the input and the output of the excitation signal, while the I port may receive a pulsed control signal to activate and deactivate the switch. DBMs have a fast switching speed and provide the required isolation between the control signal and the excitation signal. PIN diode switches may also be used. The degree to which electromagnetic interference can be suppressed depends upon the on/off ratio of the switches. A low-frequency analog switching device, such as an FET, can be employed in some applications, particularly for gating electrically downstream of the acoustic wave device.

An advantage of the present invention is that the obstacle imposed by the attenuation limit is relaxed, allowing further improvements to sensitivity. Because the electromagnetic interference is separated from the signal of interest, the electromagnetic interference cannot dominate the output of the acoustic wave device. Thus, the level of maximum tolerable attenuation is increased. Another advantage is that the invention allows the device to be more robust, since problems such as poor grounding which would otherwise increase electromagnetic interference no longer disable the sensing process.

BEST MODE FOR CARRYING OUT THE INVENTION

Figure 1:
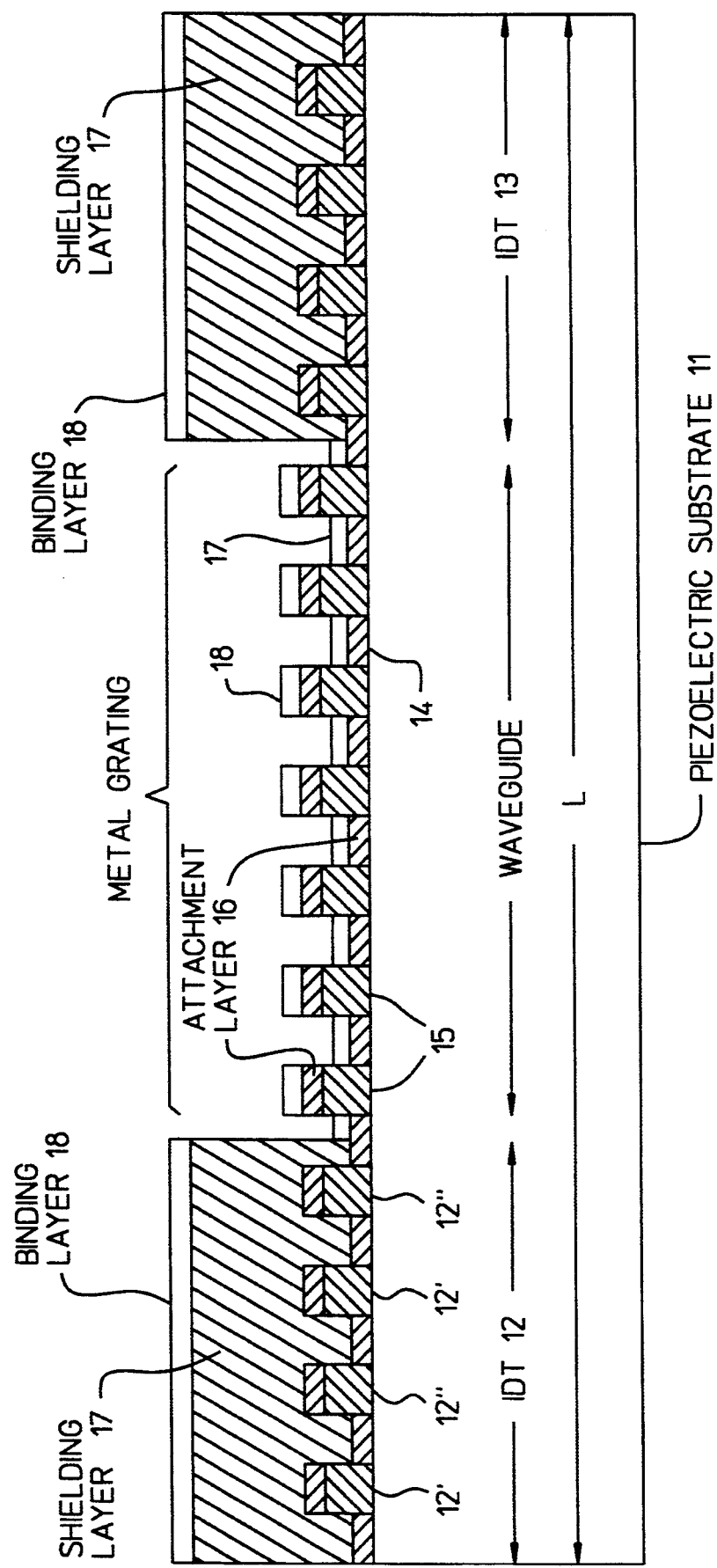
FIG. 1 is a side cross sectional view of an acoustic wave device for use as a viscosity sensor or a chemical sensor.

With reference to FIG. 1, a piezoelectric substrate 11 includes an input region having a first interdigital transducer 12 and includes an output region having a second interdigital transducer 13. The piezoelectric substrate may be made of quartz or lithium niobate, but this is not critical. Any material may be used if the material exhibits a low acoustic loss, a high dielectric constant and a high electromechanical coupling constant.

The input transducer 12 includes a first set of fingers 12' and a second set of fingers 12". An applied voltage difference between the fingers 12' and 12" produces an electric field that interacts electromechanically with the piezoelectric substrate 11. The applied voltage launches acoustic waves from the input region.

The acoustic wave device of FIG. 1 is a shear transverse wave (STW) sensor suitable for use as a viscosity sensor or a chemical sensor. Wave motion of an STW sensor is characterized by material displacement that is perpendicular to the direction of propagation and parallel to the substrate surface. Surface transverse waves tend to diffract into the bulk of the piezoelectric substrate. Thus, a grating of fingers 15 is employed along a waveguide to trap acoustic energy near the surface of the sensor. The fingers 15 are typically made of a metal, such as aluminum, gold or a metal alloy. The transducers 12 and 13 and the grating of fingers 15 are formed on the upper surface 14 of the piezoelectric substrate using conventional photolithographic techniques.

An attachment layer 16 can be deposited onto the transducers 12 and 13 and the waveguide between the transducers. The attachment layer may be silicon dioxide, which binds strongly and protects the metallic transducers and fingers from attack by chemicals. While not critical, a thick shielding layer 17 may be deposited onto the input and output regions of the piezoelectric substrate 11. The shielding layer forms a hermetic seal over the transducers 12 and 13 to protect the transducers from corrosion. The shielding layer also provides some assurance against electrical shorting of the individual fingers 12' and 12" of the transducers.

A chemically selective binding layer 18 is deposited over the waveguide of the piezoelectric substrate 11. The chemically selective binding layer 18 has a thickness on the order of a monolayer for an antibody binding layer, but may be several microns in other applications.

In operation, surface transverse waves are launched at the input interdigital transducer 12 and propagate along the waveguide. Wave-trapping fingers 15 slow the shear transverse waves, thereby creating a decay of the wave energy into the depth of the piezoelectric substrate 11. This "slowing effect" traps the acoustic wave energy closer to the upper surface 14 of the piezoelectric substrate.

Acoustic wave energy that reaches the output interdigital transducer 13 is converted to an electrical signal that is dependent upon the received wave energy. The amplitude or the phase will change from the excitation signal applied at the transducer 12 in response to the load on the layer 18. Thus, where the layer 18 is an antibody, the corresponding antigen will be captured by the layer 18. Using known measuring techniques, it is possible to quantify the antigen.

Figure 2:
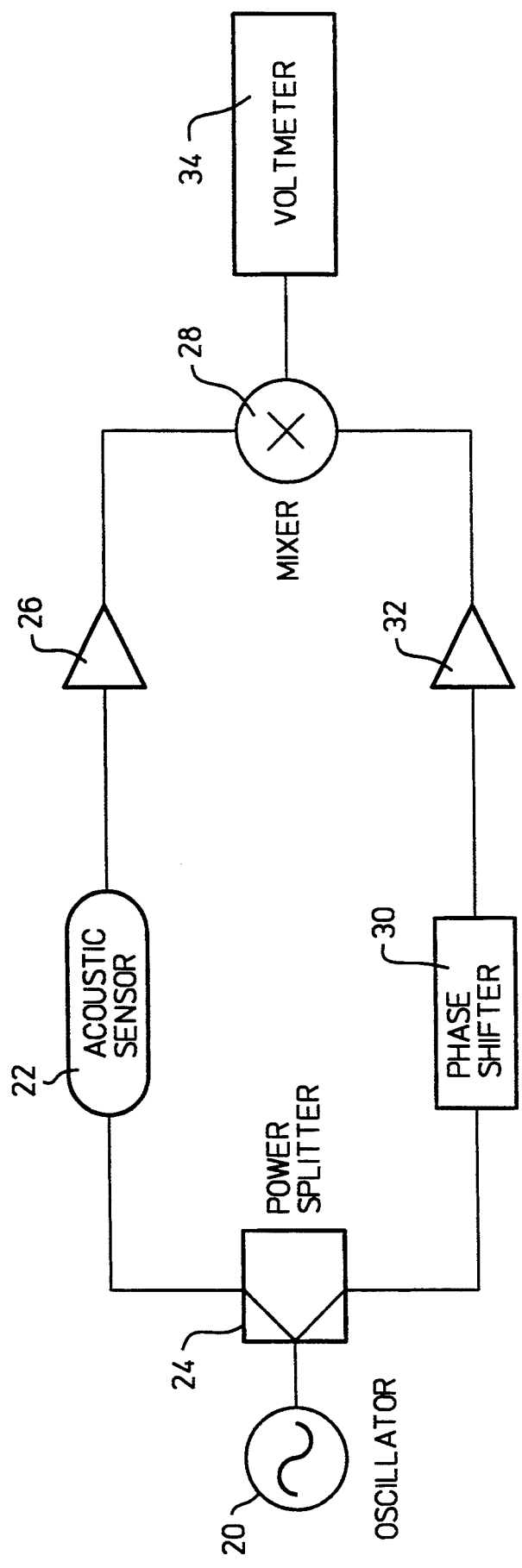
FIG. 2 is a schematical view of a radio frequency interferometer in accordance with the prior art.

A prior art measurement system is shown in FIG. 2. An interferometer is used to convert small changes in phase delay of an acoustic wave into DC voltages. An oscillator 20 generates an excitation signal, such as a 250 Mhz signal. The sensitivity of an acoustic sensor 22 increases with its frequency of operation, while the size of the sensor decreases. Therefore, acoustic sensors are operated at high frequencies.

The radio frequency (r.f.) signal from the oscillator 20 is split into two paths at a power splitter 24. One-half of the power flows to the acoustic sensor 22 to launch acoustic waves to the output transducer. The acoustic waves are converted to an electrical signal at the output transducer of the sensor. The converted electrical signal is amplified at an amplifier 26 and is channeled to an r.f. port of a double-balanced diode ring mixer 28. The remaining portion of the power of the oscillator 20 is conducted to a phase shifter 30 and then is amplified at an amplifier 32. The phase shifter is used to adjust the static phase difference across the double-balanced mixer (DBM) 28 to ninety degrees. The output of the amplifier 32 is connected to a second r.f. port of the DBM 28, so that any change in the phase length, i.e. any delay, that is caused at the acoustic sensor 22 will be converted directly into a DC voltage by the DBM. This DC voltage can then be measured using a voltmeter 34.

Referring now to FIGS. 1 and 2, a difficulty with the measurement system described above is that in addition to the coupling of acoustic energy from the input interdigital transducer 12 to the output interdigital transducer 13, there is direct electromagnetic coupling between the transducers 12 and 13. A first source of the direct coupling is electromagnetic radiation. The input interdigital transducer 12 will act as a transmitter, while the output transducer 13 functions as a receiver of electromagnetic radiation. Thus, there is a coupling of energy that does not undergo acoustic conversion. A second source of the direct electromagnetic coupling involves inter-transducer capacitance. The electromagnetic radiation and the capacitive coupling between the transducers each contribute to "electromagnetic interference."

When the acoustic wave device is employed as a delay line for sensing, the attenuation suffered by propagating acoustic waves may be large. High attenuation may be a result of the binding layer 18 attached to the sensor to provide preferential capture. Once the attenuation becomes sufficiently large, the acoustic component of the signal from the output transducer 13 falls below the level of the directly coupled electromagnetic interference. When this occurs, the output signal is determined only by the directly coupled electromagnetic signal, effectively rendering the sensor inoperative.

The present invention prevents dominance of the electromagnetic interference by taking advantage of the difference in speeds of the directly coupled energy and the acoustic wave propagation. The electromagnetic interference travels at the speed of light, while the acoustic waves travel through the STW device at the speed of sound in solids. The electromagnetic interference therefore travels at a speed roughly five orders of magnitude greater than the acoustic wave. For example, the acoustic waves through the STW delay line may have a velocity of 5000 m/s across the waveguide length (L) of 1 cm. At this rate, the acoustic signal arrives at the output 2 microseconds after the arrival of the directly coupled electromagnetic interference. By pulsing the excitation signal to the input transducer 12, and by gating the output signal from the output transducer 13, the output signal components of electromagnetic interference and acoustic wave-generating energy can be separated. The electromagnetic interference can then be eliminated.

Figure 3:
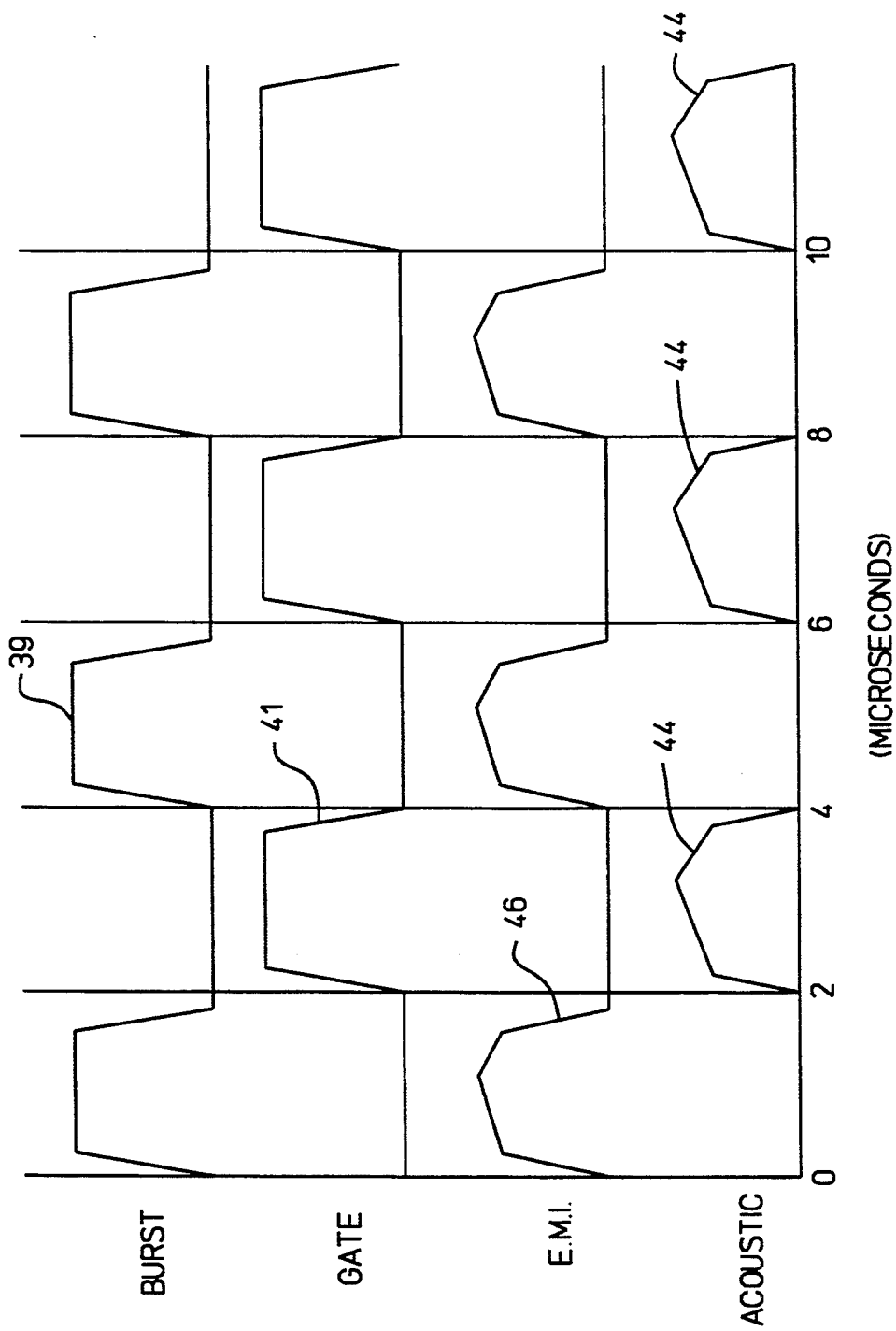
FIG. 3 is a timing diagram for operation of an interferometer in accordance with the present invention.
Figure 4:
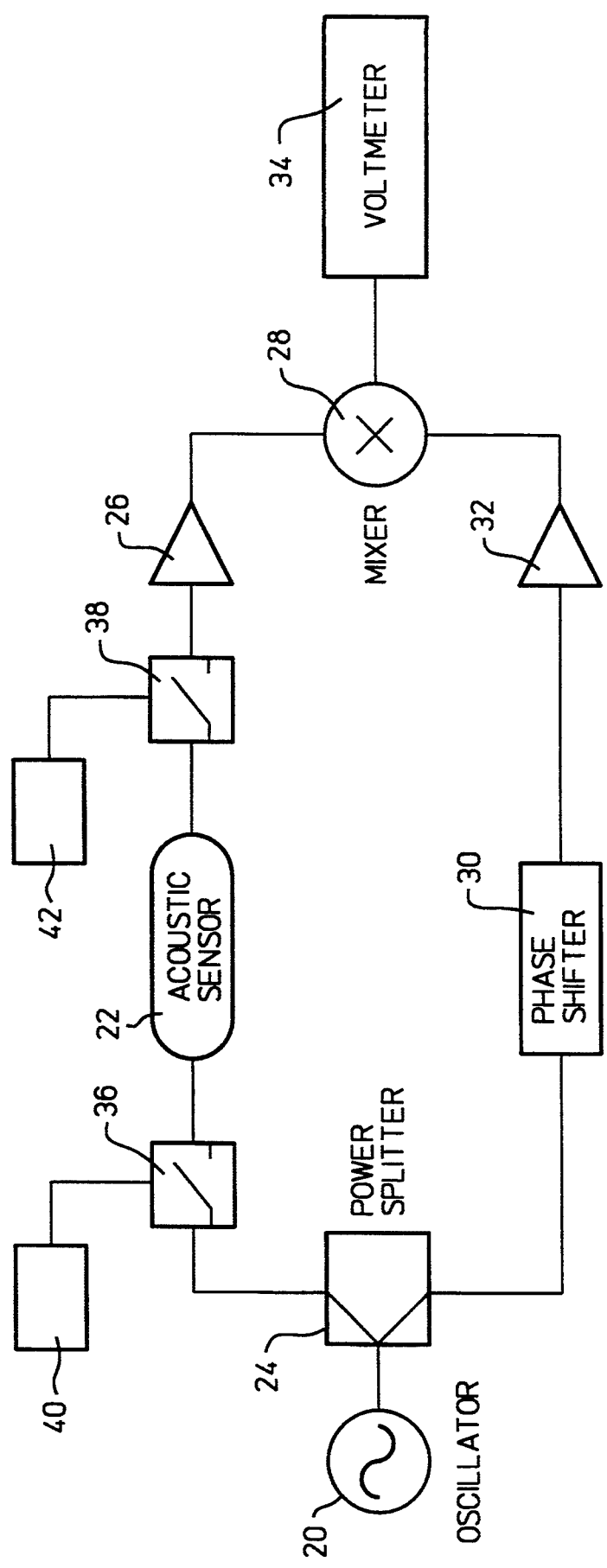
FIG. 4 is a schematical view of the first embodiment of a radio frequency interferometer having an acoustic sensor such as the device of FIG. 1 and having input and output switches in accordance with the present invention.

Referring now to FIGS. 3 and 4, a first embodiment of the invention is shown as including each of the components of a prior art interferometer. These components include the oscillator 20, power splitter 24, acoustic sensor 22, amplifiers 26 and 32, phase shifter 30, mixer 28 and the voltmeter 34. In addition to the conventional components, the first embodiment includes a burst switch 36 and a gate switch 38. A pulse train 39 to the burst switch 36 is generated at a source 40 and is shown in FIG. 3. A "high" from the source 40 closes the burst switch 36 to allow passage of an excitation signal to the acoustic sensor 22. A "low" from the source 40 to the burst switch opens the switch, as shown in FIG. 4.

The gate switch 38 is operated by a signal 41 from a source 42. The signal is seen in FIG. 3 to comprise a series of pulses. A high closes the switch, while a low from the source opens the switch.

The burst switch 36 and the gate switch 38 are r.f. switches that modulate the excitation signal and gate the acoustic component of the sensor 22. The first switch 36 is referred to as a burst switch, since it converts the excitation signal into a series of r.f. bursts. The second switch 38 is referred to as a gate switch, since it gates out the undesired components of the sensor output.

The r.f. switches are driven in a particular manner in order to eliminate electromagnetic interference. The burst switch is driven by the source 40 with pulses that are each shorter in length than the acoustic delay of the sensor 22. Therefore, if the acoustic delay is 2 microseconds, the duration of the pulses from the source 40 should be less than 2 microseconds. Ideally, the burst switch 36 is driven by a pulse that is only slightly shorter than the acoustic delay period, thereby maximizing the percentage of time for which the sensor 22 is launching acoustic waves. The pulses from the source 40 are shorter than the length of the acoustic delay, since continuing to launch acoustic waves at the input transducer while the output transducer is receiving acoustic waves will result in simultaneous arrival of electromagnetic interference and acoustic wave energy.

The period of the pulses from the source 40 to the burst switch 36 must be greater than the sum of the acoustic delay of the sensor 22 and the duration of the burst pulses. This allows time for the last launched acoustic wave of the first r.f. burst from the oscillator 20 to reach the output transducer of the sensor before the next r.f. burst from the oscillator 20 is initiated. In this manner, the simultaneous arrival of the two components of signal outputs does not occur.

Regarding the gate signal from the source 42, the pulses must be timed to close the gate switch 38 during periods in which acoustic wave energy 44 is at the output transducer of the sensor 22. The gate switch 38 should be allowed to open during periods in which electromagnetic interference 46 is expected at the output of the sensor 22. Thus, a high from the source 42 should not coincide with a high from the source 40. While the gate switch 38 is important in the interferometer of FIG. 4, the present invention may be utilized without such a switch if measuring apparatus connected to an acoustic wave device is not sensitive to the separated interference, Likewise, it may be possible to provide other means of offsetting the electromagnetic interference after the burst switch 36 has provided separation of the two components of sensor output.

Referring to FIG. 3, the first pulse 46 at the output of the acoustic transducer is virtually undelayed, since it is associated with electromagnetic interference that travels at the speed of light. The second pulse 44 is delayed, since acoustic propagation will travel much slower than electromagnetic radiation. The relative amplitudes of the two sets of pulses 44 and 46 depend on the level of electromagnetic interference and the degree of acoustic attenuation through the sensor. Dispersion may cause the shape of the pulses associated with the acoustic wave energy 44 to be different from the electromagnetic pulses 46.

The burst switch 36 and the gate switch 38 may be of a variety of types. One preferred type of switch is a double-balanced diode ring mixer (DBM) identical to the mixer 28. The L and R ports of the mixer may be used as signal inputs and outputs connected to the acoustic sensor 22, while the I port is connected to the associated source 40 and 42. DBMs have an acceptable switching speed and provide excellent isolation between the driving pulses and the signals channeled to and from the acoustic sensor 22. However, DBMs exhibit a significant "on" state insertion loss of approximately 4 dB, and can handle only a limited amount of power.

Alternatively, PIN diode switches have been employed. PIN diode switches are somewhat slower than DBM switches, but the PIN diode switches can handle very high power levels with a low level of loss. As a third alternative, a low-frequency analog switching device, such as an FET, can be used as a gate switch in certain applications. The degree to which electromagnetic interference can be suppressed depends upon the on/off ratio of the burst and gate switches 36 and 38. DBM and PIN diode switches can provide on/off ratios of greater than 30 dB with microsecond switching speed. All of the above-identified switching devices are commercially available. An acceptable DBM is sold by Mini-Circuits, Inc. under the model number ZFM-2. A PIN diode switch is available from Signetics under the model number NE-630. A baseband switch is available from Analog Devices under the model number AD201HS.

Figure 5:
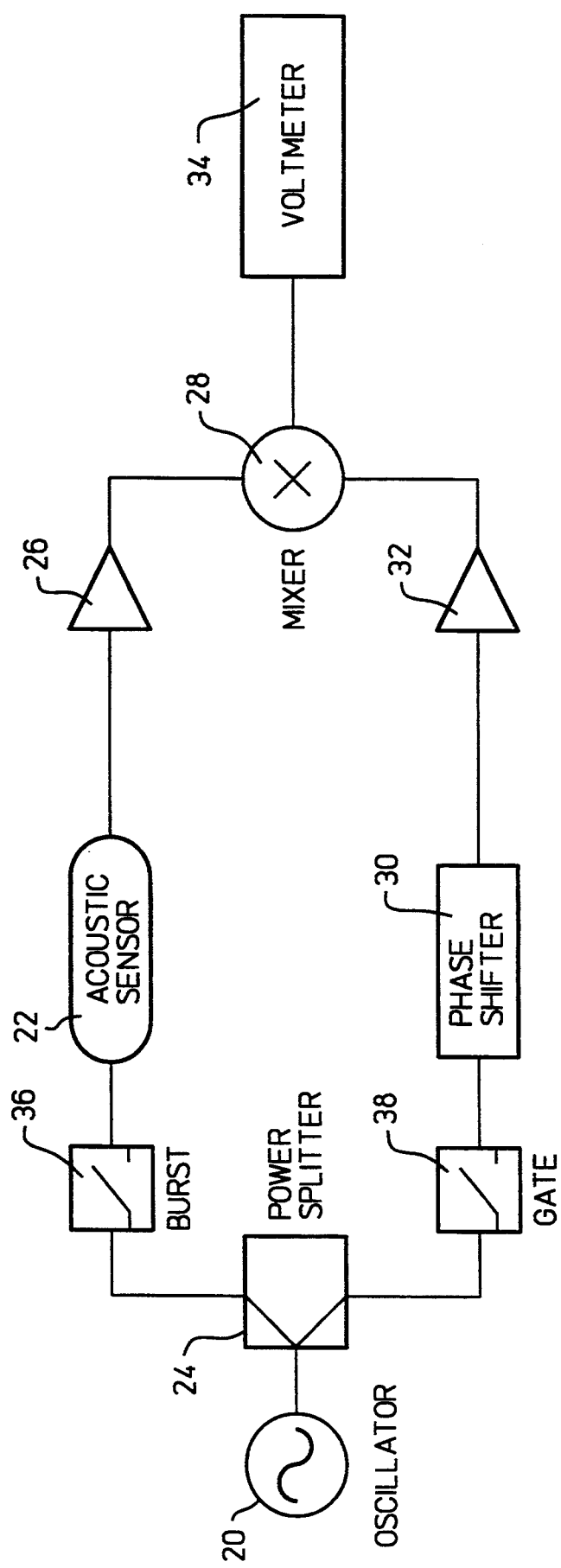
FIGS. 5–9 are alternate embodiments of the interferometer of FIG. 3.

FIGS. 5-9 illustrate alternate embodiments of invention. The embodiments of FIGS. 5 and 6 include all of the components of FIG. 4, but the positioning of the gate switch 38 is changed. In FIG. 5, the gate switch 38 is positioned to take advantage of the fact that the mixer 28 in the interferometer produces no output to the voltmeter 34 unless signals are simultaneously presented at the opposed ports from the amplifiers 26 and 32.

Figure 6:
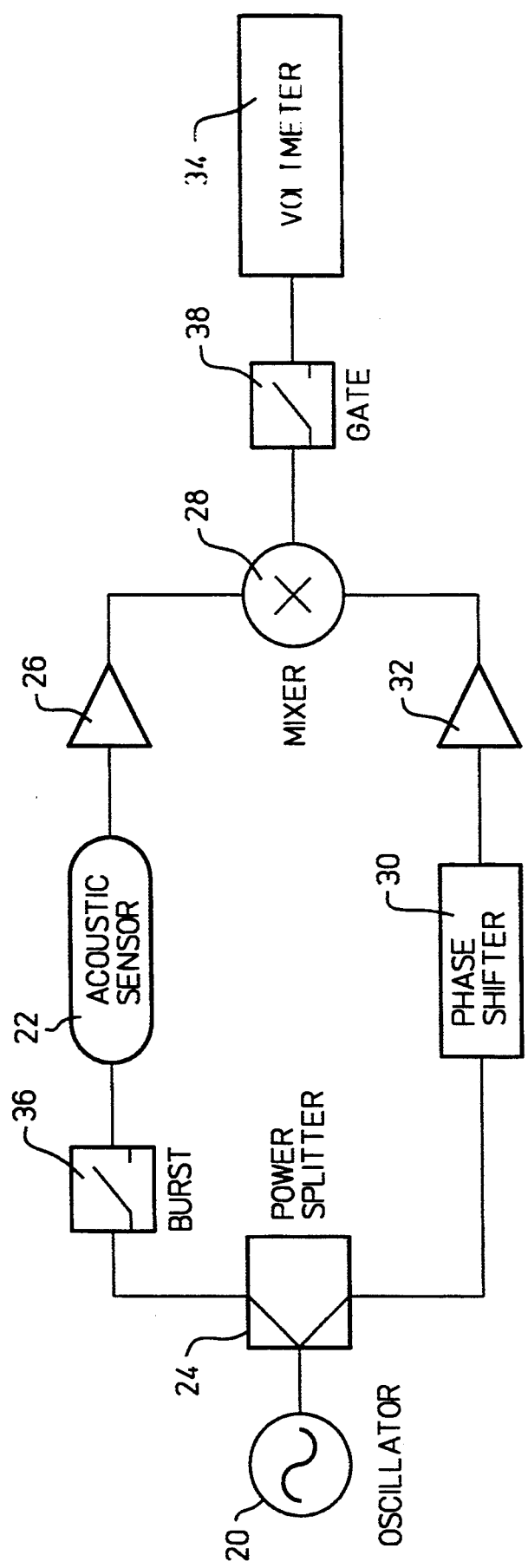

In FIG. 6, the gate switch 38 is positioned between the mixer 28 and the voltmeter 34, so that the voltmeter is disabled during those times in which electromagnetic interference determines the output of the mixer 28.

Figure 7:
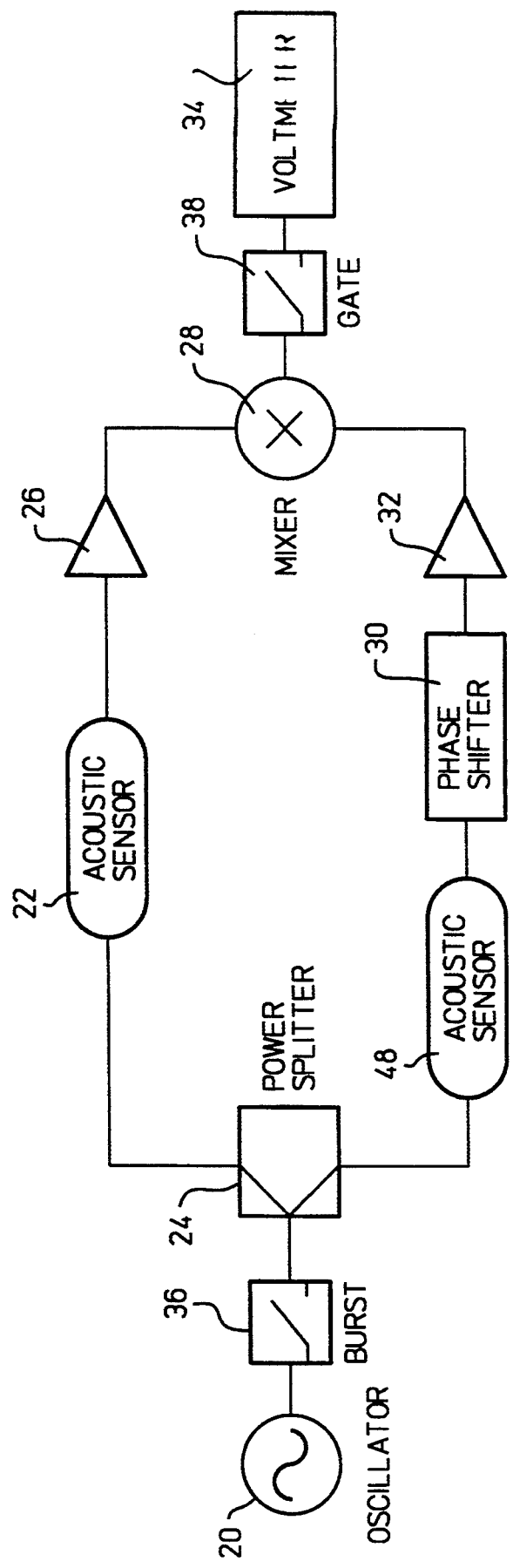
Figure 8:
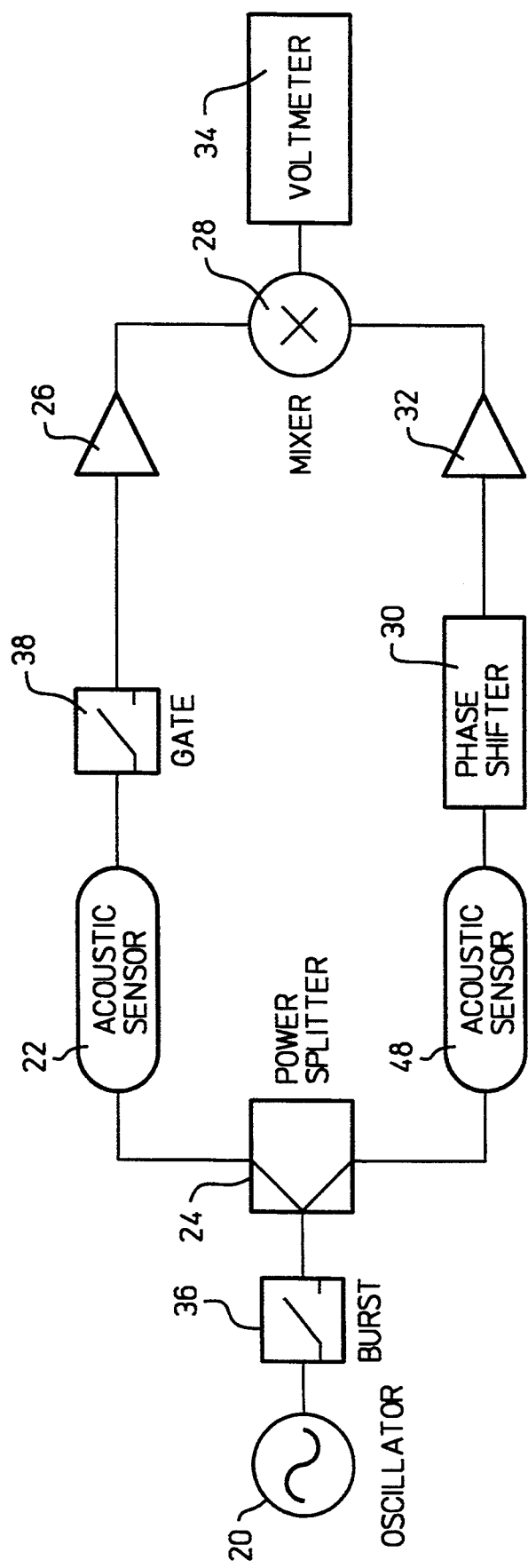
Figure 9:
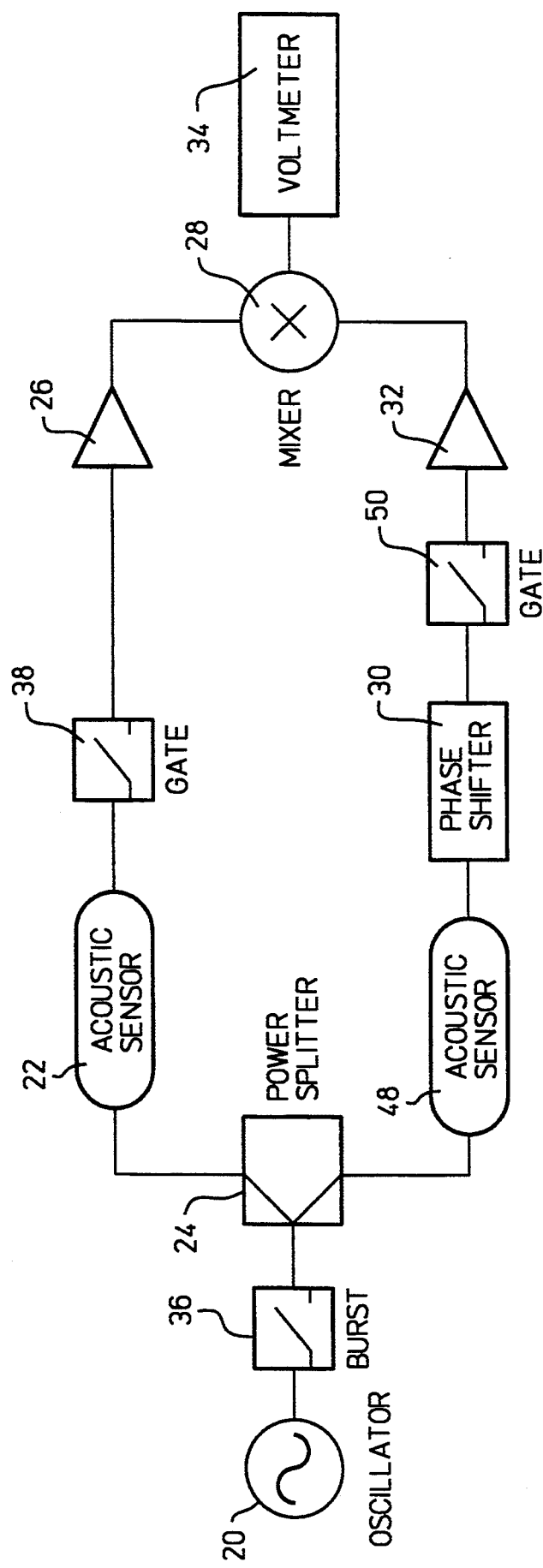

Dual sensor interferometers are shown in FIGS. 7-9. The second sensor 48 is connected in parallel with the first sensor 22. For these embodiments, the burst switch 36 is positioned between the oscillator 20 and the power splitter 24, thereby allowing the separation of electromagnetic interference and acoustic wave-generated energy at both of the sensors 22 and 48. The gate switch 38 can be repositioned. In FIG. 7, the gate switch 38 is located between the mixer 28 and the voltmeter 34. The gate switch disables the voltmeter during periods of launching acoustic waves across the sensors 22 and 48, but the gate switch is closed during periods in which acoustic waves are received at the output of the sensors.

In FIGS. 8 and 9, a gate switch 38 and 50 is connected along at least one of the parallel paths to the mixer 28. Because an ideal mixer will produce no output signal unless signals are simultaneously present from amplifiers 26 and 32, the voltmeter is insensitive to electromagnetic interference. FIG. 9 includes a second gate switch 50 to gate out any residual output due to mixer imbalance.

While the present invention has been described as being used with an interferometer, the method of operating an acoustic wave device to separate desired and undesired components of the device output may be employed in other applications and with the various types of acoustic wave devices. That is, the invention may be utilized with any acoustic wave device which is affected by electromagnetic interference at an output region of the device.

I claim:

1. A method of operating an acoustic wave device comprising,
    providing a substrate for the propagation of acoustic waves from an input region to an output region,
    applying excitation energy singly to the input region such that acoustic conversion of the excitation energy launches acoustic wave energy from the input region,
    forming an electrical signal in response to energy detected at the output region, and
    maintaining a separation of each period of arrival of acoustic wave energy at the output region from each period of arrival of undesired non-acoustic wave energy that is coupled from the input region to the output region without undergoing acoustic conversion, including selectively interrupting the application of the excitation energy to the substrate based upon the time required for acoustic wave energy to travel from the input region to the output region and further based upon continuously averting simultaneous arrival of the acoustic wave energy and the non-acoustic wave energy at the output region.

2. The method of claim 1 wherein separating the periods of arrival of acoustic and non-acoustic energy includes limiting the application of the excitation energy singly to the substrate to time intervals of less than the required time for acoustic wave energy to travel from the input region to the output region.

3. The method of claim 2 wherein separating the periods of arrival of acoustic and non-acoustic wave energy includes periodically interrupting the application of the excitation energy singly to the substrate for a duration at least as great as the sum of the time interval and the required time for acoustic wave energy to travel from the input region to the output region.

4. The method of claim 1 further comprising periodically gating the electrical signal formed in response to energy detected at the output region, the gating including interrupting an electrical path from the output region during periods in which non-acoustic energy is received at the output region.

5. The method of claim 4 wherein separating the periods of arrival of acoustic and non-acoustic wave energy includes providing a first electrical switch to the input region and wherein gating the electrical signal includes providing a second electrical switch from the output region, the method further comprising generating radio frequency control signals to activate and deactivate the first and second electrical switches.

6. An acoustic wave device comprising,
    a substrate means for propagating acoustic waves across a propagation region, the substrate means having input and output regions on opposed sides of the propagation region,
    input means for applying an excitation signal to the substrate means solely at the input region, thereby launching acoustic waves across the propagation region,
    output means for forming an electrical signal in response to energy at the output region of the substrate means, the energy at the output region including acoustic energy from the propagation region and—including electromagnetic energy coupled from the input means,
    energy-separation means for continuously isolating the acoustic energy at the output region from the electromagnetic energy, the energy-separation means including means for limiting the application of the excitation signal by the input means to intervals of less than the time of travel of the acoustic waves from the input region to the output region, and including means for interrupting the application of the excitation signal by the input means to intervals of time at least as great as the time of travel of acoustic waves from the input region to the output region, and
    gating means for continuously isolating a component of the electrical signal formed in response to the acoustic energy from a component of the electrical signal formed in response to the electromagnetic energy, the gating means being electrically coupled to the output means.

7. The device of claim 6 wherein the energy-separation means includes a source of periodic pulses, the source being in electrical communication with the input means to activate and deactivate the application of the excitation signal.

8. The device of claim 7 wherein the energy-separation means includes a switch responsive to the source of periodic pulses.

9. The device of claim 8 wherein the switch is one of a double-balanced mixer and a PIN diode.

10. The device of claim 6 wherein said gating means selectively gates the electrical signal formed by the output means in response to the time of travel of the acoustic waves from the input region to the output region, the gating means having an input, the input being in electrical connection with an output of the output means.

11. The device of claim 10 further comprising means for monitoring changes of one of amplitude and phase of acoustic waves and the gating means further having an output, the output being in electrical connection with the monitoring means.

12. The device of claim 6 wherein the gating means has an input and an output, the input being in electrical connection with the output region of the substrate means, the output being in electrical connection with the input of the output means.

13. An acoustic delay device comprising, a piezoelectric substrate having a propagation region, an input transducer on a first side of the propagation region for converting electrical energy into acoustic wave energy, a source of electrical energy selectively coupled to the input transducer, first switch means for selectively interrupting conduction of electrical energy from the source to the input transducer based upon speed of travel of the acoustic wave energy through the piezoelectric substrate, an output transducer on a second side of the propagation region for converting acoustic wave energy into electrical energy, means for monitoring one of phase and amplitude of electrical energy from the output transducer, and second switch means for selectively interrupting the conduction of electrical energy from the output transducer to the means for monitoring based upon the speed of travel of the acoustic wave energy through the piezoelectric substrate.

14. The device of claim 13 further comprising a first controller source of control pulses connected to the first switch means so as to periodically activate and deactivate the first switch means.

15. The device of claim 14 wherein the first controller source generates pulses for activating the first switch means such that electrical energy is coupled to the input transducer for durations less than the required time for the acoustic wave energy to travel from the input transducer to the output transducer.

16. The device of claim 15 wherein the first controller source generates pulses having a period at least as great as the sum of the required time for the acoustic wave energy to travel from the input transducer to the output transducer and the time that the first switch means is activated.

17. The device of claim 15 wherein the first switch means is one of a double-balanced mixer and a PIN diode.

18. The device of claim 15 further comprising a second controller source of control pulses connected to the second switch means so as to periodically activate and deactivate the second switch means, including deactivating the second switch means whenever the first switch means is activated.

19. A method of operating an acoustic wave device comprising, providing a substrate for the propagation of acoustic waves from an input region to an output region, applying excitation energy to the input region such that acoustic conversion of the excitation energy launches acoustic wave energy from the input region, forming an electrical signal in response to energy detected at the output region, separating the arrival of acoustic wave energy at the output region from the arrival of undesired non-acoustic wave energy that is coupled from the input region to the output region without undergoing acoustic conversion, including selectively interrupting the application of the excitation energy to the input region based upon the time required for acoustic wave energy to travel from the input region to the output region, and monitoring the electrical signal formed in response to acoustic wave energy detected at the output region, the monitoring including sensing changes in one of amplitude and phase of the acoustic wave energy.

* * * * *